United States Patent [19]

Whistler

[11] 4,413,120
[45] Nov. 1, 1983

[54] PROCESS FOR PRODUCING ACOSAMINE, DAUNOSAMINE, 1-THIOACOSAMINE AND RELATED COMPOUNDS

[75] Inventor: Roy L. Whistler, West Lafayette, Ind.

[73] Assignee: Purdue Research Foundation, Lafayette, Ind.

[21] Appl. No.: 251,636

[22] Filed: Apr. 6, 1981

[51] Int. Cl.³ .............................................. C07H 1/00
[52] U.S. Cl. .................................. 536/18.6; 536/17.2; 536/17.5; 536/18.5; 536/55.3; 536/6.4
[58] Field of Search ....................... 536/1, 4, 18, 17 A, 536/4.1, 1.1, 17.5, 18.5, 18.6, 17.2, 55.3

[56] References Cited

U.S. PATENT DOCUMENTS 4,166,848 9/1979 Bernardi et al. ................... 536/17 A
4,181,795 1/1980 Whistler ............................ 536/17 A
4,201,773 5/1980 Horton et al. ..................... 536/17 A

OTHER PUBLICATIONS

Stanek et al., "Monosaccharides", Academic Press, N.Y., NY 1963.
Pelyvas and Whistler, "Synthesis of L-Acosamine and 1-Thio-L-Acosamine Derivatives by the Stereoselective Reduction of O-Acetyloximes with Borane," *Carbohydrate Research*, 84 (1980) C5-C7.
Sztaricskai et al., "A Synthesis of 1-Ristosamine and a Derivative of Its C-4 Epimer," *Carbohydrate Research*, 65 (1978), 193-200.
Pelyvas et al., "A Convenient New Route to Methyl N,O-Diacetyl-α-L-Ristosaminide," *Carbohydrate Research*, 76 (1979), 257-260.

*Primary Examiner*—Johnnie R. Brown
*Attorney, Agent, or Firm*—Biebel, French & Nauman

[57] ABSTRACT

A process for synthesizing acosamine, daunosamine and 1-thioacosamines from L-rhamnal is disclosed that can generally be characterized by Michael addition of an alkoxide or thioalkoxide to the enone formed by allylic oxidation of L-rhamnal to directly generate the 2-deoxy functionality, and stereospecific reduction of the oxime to the arabino compound which establishes configuration at C-3 and generates a compound which requires only epirmerization at C-4 to yield the desired product. The synthesis of anthracycline antibiotics incorporating these sugars or their derivatives by glycosidation of the glycone is also disclosed.

6 Claims, No Drawings

PROCESS FOR PRODUCING ACOSAMINE, DAUNOSAMINE, 1-THIOACOSAMINE AND RELATED COMPOUNDS

BACKGROUND OF THE INVENTION

Broadly, the present invention relates to the synthesis of acosamine, daunosamine and 1-thioacosamines and derivatives thereof. More particularly, it relates to their syntheses as they apply to the synthesis of anthracycline antibiotics such as doxorubicin, daunorubicin and carminomycin.

Anthracycline antibiotics have been found effective in treating a wide variety of cancers including acute myeloblastic and lymphoblastic leukemia. It has been found that these antibiotics are glycosides formed of a tetracyclic aglycone and a 3-amino-2,3,6 trideoxy sugar and can be represented by the formula:

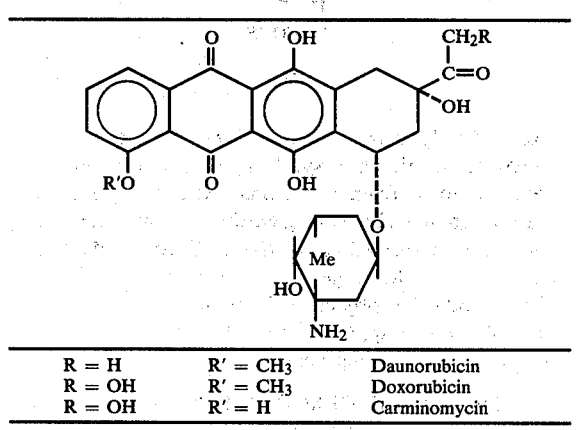

| R = H | R' = $CH_3$ | Daunorubicin |
| R = OH | R' = $CH_3$ | Doxorubicin |
| R = OH | R' = H | Carminomycin |

The antibiotic doxorubicin is the subject of U.S. Pat. No. 3,590,028 and is available as the hydrochloride under the label "Adriamycin" ™ from Adria Laboratories, Inc., Dublin, Ohio. Adriamycin ™ has been used successfully to produce regression in several carcinoma and disseminated neoplastic conditions and is a prescribed antineoplast.

Conventionally, anthracycline antibiotics are produced by aerobic fermentation of strains of Streptomyces. These conventional fermentation processes are inefficient and expensive. Furthermore, there has been a desire to study the effects of analogues of these antibiotics and they are not available through fermentation and are virtually impossible to obtain by modification of the fermentation products. Accordingly, efforts have been directed to developing effective synthetic routes to these compounds.

One synthesis which has been treated somewhat extensively in the literature provides the antibiotics in good yields by coupling a separately prepared aglycone and amino sugar. Using this process it is also possible to individually modify the aglycone and amino sugar and thereby obtain access to a variety of derivatives. Under this approach, for example, daunorubicin and doxorubicin have been prepared by glycosidation of daunomycinone and adriamycinone, respectively, with daunosamine.

Although daunosamine has been synthesized before for one reason or another, the syntheses have not been satisfactory. In one particular case, Marsh et al., Chem. Commun. (1967) 973-75, synthesize daunosamine from L-rhamnose by a technique which requires chromatographic separation of the product. This technique does not provide the compounds in effective amounts and yields.

U.S. Pat. No. 4,024,333 discloses the synthesis of daunosamine from D-mannose. The characteristic feature of this approach involves formation of a 2-deoxy-3-keto intermediate, whose oxime is reduced with high stereoselectivity to the D-ribo-3-amino compound, followed by a stereospecific step late in the sequence to introduce a terminal C-methyl group with inversion at C-5 to generate the required L-lyxo stereochemistry.

A synthesis has been developed for the daunosamine stereoisomer, L-ristosamine, from L-rhamnal by a sequence of reactions involving methoxymecuration, tosylation, azide displacement and reduction to yield methyl-L-ristosaminide. Acid hydrolysis affords the L-ristosamine hydrochloride. However, the methoxymercuration step is undesirable because it involves reagents which are not only expensive, but toxic and, consequently, unsatisfactory for industrial applications. Furthermore methoxymercuration is incapable of adding a thioalkyl group to the starting sugar and therefore can not yield 1-thioacosamines. Accordingly, there still exists a need in the art for an effective synthesis for daunosamine and 1-thioacosamine in which chromatographic techniques are not required and which does not involve the expense and toxicity of methoxymercuration.

SUMMARY OF THE INVENTION

In accordance with the present invention, acosamine, daunosamine and 1-thioacosamines are prepared from L-rhamnal by a process that can generally be characterized by Michael addition of an alkoxide or thioalkoxide to the enone formed by allylic oxidation of L-rhamnal to directly generate the 2-deoxy functionality, and stereospecific reduction of the oxime to the arabino compound which establishes configuration at C-3 and generates a compound which requires only epimerization at C-4 to yield the desired product. More specifically, the present invention is directed to the synthesis of daunosamine and 1-thioacosamines and to the synthesis of anthracycline antibiotics incorporating these sugars or their derivatives by glycosidation of the aglycone.

The process of the present invention will be described in more detail by reference to the following diagram of the involved rections in which Bn=benzyl, Ac=acetate, Me=methyl and THF=tetrahydrofuran. In the discussion which follows, the products and intermediates generated in the syntheses will be identified by reference to the compounds as numered below.

Synthesis of Acosamine and Daunosamine

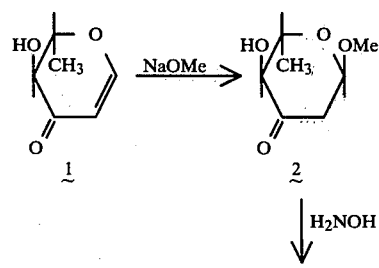

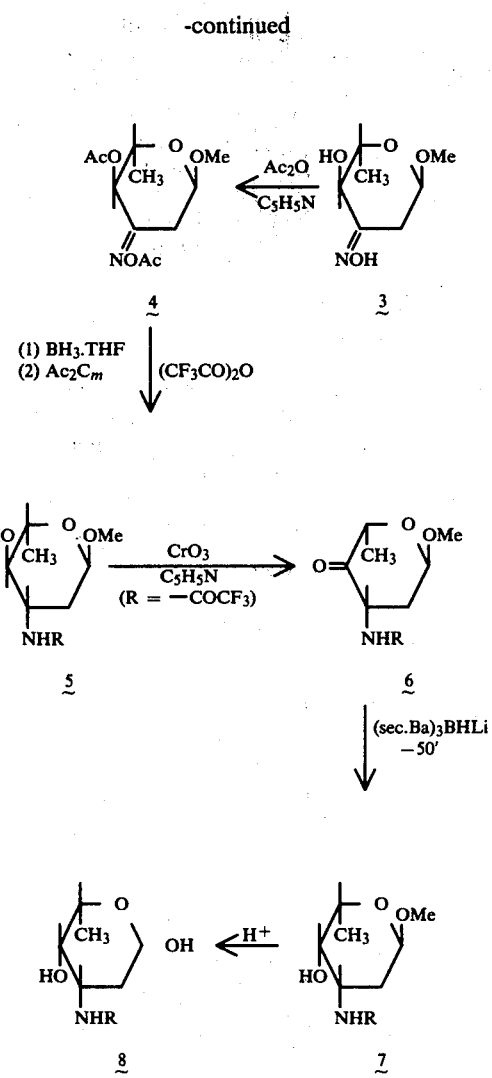
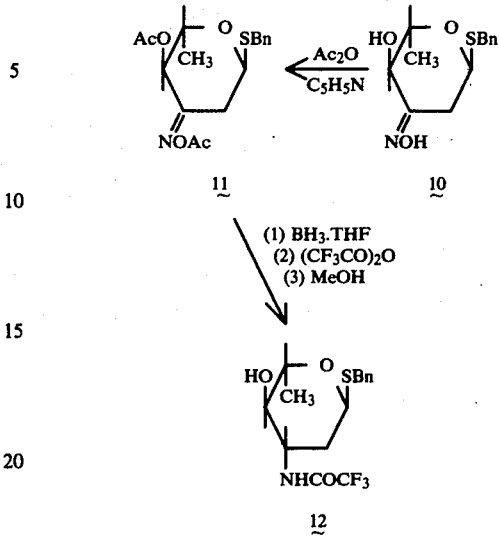

Synthesis of 1-Thioacosamine

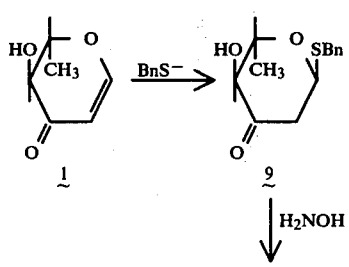

Accordingly, it is an object of the present invention to provide an effective synthesis of daunosamine and 1-thioacosamine from L-rhamnal which provides the sugars in good yields and quantities. Acosamine is obtained as an intermediate in the synthesis of daunosamine and is another object of the present invention.

These and other objects and advantages of the invention will become apparent from the following description and accompanying claims.

DETAILED DESCRIPTION OF THE INVENTION

I. Synthesis of Acosamine and Daunosamine

A. Allylic oxidation of L-rhamnal

The starting material for these syntheses of daunosamine and the thioacosamines is the enone 1 (1,5 anhydro-2,6-dideoxy-L-erythro-hex-1-en-3-ulose) obtained by allylic oxidation of L-rhamnal. This allylic oxidation is preferably accomplished with Fetizon's reagent ($Ag_2CO_3$/celite) but can also be performed with chromium trioxide:pyridine complex or manganese dioxide.

When Fetizon's reagent is used, L-rhamnal is dissolved in benzene and then the Fetizon's reagent is added to the mixture (20 g reagent: 1 g L-rhamnal). The mixture is refluxed for 1 hour, the spent reagent removed by filtration, and the solvent removed by evaporation to yield nearly pure enone. When the oxidant is chromium trioxide:pyridine complex, L-rhamnal is added to a solution of the oxidant in dichloromethane followed by addition of 4 equivalents of acetic anhydride. After 20 minutes the reaction mixture is poured onto a column of silica gel (ethyl acetate eluent) containing excess ethyl acetate at the top to precipitate insoluble chromium compounds. The product is eluted with ethyl acetate. If manganese dioxide is used, L-rhamnal is dissolved in tetrahydrofuran and treated with active manganese dioxide (15 g $MnO_2$: 1 g L-rhamnal) and stirred at room temperature for 2-3 days. The oxidant is then removed by filtration and the product purified by chromatography on a silica gel column (ethyl acetate eluent).

B. Michael addition of alkoxide

A Michael-type addition of the methyl glycoside to the enone 1 yields the methyl glycoside 2-deoxy-3-ulose 2 (methyl 2,6 dideoxy α-L-erythrohexopyranosid-3-ulose).

Generally, Michael additions require highly activated olefins and strong nucleophiles. However, it has recently been shown that the enone, 1,5-anhydro-2,6-dideoxy-L-erythro-hex-1-en-3-ulose, will undergo a Michael-type addition with sodium methoxide to yield the 2-deoxy methyl glycoside (Pelyvas et al., *Carhohydrate Research*, 76 ((1979)) 257-260). The reaction is almost completely stereospecific, resulting in an α:β ratio of 15:1.

In some Michael-type additions of alkoxides to carbohydrate enones both 1,2- and 1,4-additions have been observed. Thus, in the above reaction sequence, some addition of methoxide at C-3 might be expected. It has been found, however, that the Michael addition product consists almost entirely of Compound 2. This is believed to be due to the fact that the 1,2 addition of alkoxide at C-3 is reversible whereas the 1,4 addition at C-1 as in Compound 2 is not. Thus the reaction is almost exclusively a 1,4 addition yielding Compound 2.

Michael addition of methoxide is readily accomplished by reacting the enone with a dilute base, particularly sodium methoxide, in methanol (0.10 M) for 10 minutes. The mixture is then neutralized with a cation-exchange resin, filtered and evaporated to yield Compound 2.

C. Oximation

Treatment of compound 2 with an excess of hydroxylamine produces the desired 2-deoxy-3-oximino compound 3. This reaction is generally performed by reacting Compound 2 dissolved in a lower alcohol (e.g. methanol, ethanol) with a solution containing a 5-6 fold excess of hydroxylamine in the same lower alcohol. The hydroxylamine solution is prepared by reacting equimolar amounts of hydroxylamine hydrochloride and potassium hydroxide in a lower alcohol. The reaction is typically conducted at room temperature for 4-8 hours after which time the reaction mixture is evaporated to give a syrup containing mostly Compound 2.

D. Stereospecific reduction of the oxime

Stereospecific reduction of the oxime is a crucial step in the success of the reaction sequence. Previous work reported by Pelyvas et al. in *Carbohydrate Research*, supra. has shown that Raney nickel reduction of the oxime yields the ribo compound (a derivative of ristosamine) in admixture with the arabino compound (a derivative of acosamine). Therefore, in some prior syntheses in which the acosamine is desired, the arabino compound must be isolated from the ribo compound before the end product desired can be attained. This results in a coincidental reduction in yield. Experimentation with numerous reducing agents has led to the discovery that the oxime or the O-acetyl oxime (Compound 3 or 4) can be stereospecifically reduced with a borane-THF complex to an arabino configuration. The importance of this discovery is that it establishes the configuration at C-3 and generates the acosamine in good yield.

A typical stereospecific reduction involves dissolving Compound 4 in dry THF and cooling to 0° C. A solution of Borane in THF is added over a period of 30 minutes. The solution is stirred at 0°-5° C. for 1 hour and then refluxed for 1.5 hours. The mixture is then allowed to stand at room temperature for 18 hours. Treatment of the mixture with hot alkali followed by extractive isolation yields methyl L-acosaminide.

Stereospecific reductions of oximes using borane have been known but not for the type sugars used herein. Previously Rosenthal and Catsoulacos, *Canada J. Chem*, 47 (1969) 2747-50 reported the reduction of a C-3 oxime of a 2,3 dideoxy sugar with borane, to obtain a 3:1 mixture of the arabino and ribo compounds. Lemieux et al, *Canada J. Chem.*, 51 (1973) 33-41 also reduced a 2-amino-2-deoxy sugar to the glucopyranoside as opposed to the manno with high selectivity using borane.

F. Epimerization of C-4

Epimerization of the C-4 acosamine yields daunosamine. This and the subsequent steps in this synthesis convert the acosamine to the daunosamine by epimerization of C-4. Usually this is accomplished by sequentially protecting the nitrogen atom, oxidizing the hydroxy group at C-4 to produce the 4-ulose and reducing the 4-ulose to the lyxo derivative.

(i) Protecting the Nitrogen

The reduction product of Compound 4 is directly N-trifluoroacetylated to produce the amido glycoside 5 whereby the nitrogen is protected by reacting with the trifluoroacetic acid in ethyl ether. This results in di-trifluoroacetylation of compound 4, i.e., the di-N,O-trifluoroacetylated compound. The product is treated with methanol to cause cleavage of the O-ester, but not the N-amide. While other means may be adapted for protecting the nitrogen group throughout the subsequent reactions, trifluoroacetyl is preferred for the exceptional ease with which the ester can be cleaved and the relative ease of cleavage of the amide.

(ii) Oxidation of Glycosides

Oxidation of the glycoside 5 with chromium trioxide:pyridine complex cleanly produces the 4-ulose, Compound 6. This reaction can be accomplished by adding Compound 5 to a solution of the chromium oxide:pyridine complex in dichloromethane followed by addition of 4 equivalents of acetic anhydride. After 10-20 minutes the reaction mixture is poured onto a column of silica gel (ethyl acetate eluent) containing excess ethyl acetate at the top to precipitate insoluble chromium compounds. The product is eluted with ethyl acetate.

(iii) Reduction of the 4-ulose

Careful experimentation with numerous reducing agents has led to the discovery that lithium tri(sec-butyl) borohydride will stereospecifically tri(sec-butyl) borohydride will stereospecifically reduce the 4-ulose, 6, to the L-lyxo derivative 7. Compound 6 is dissolved in dry THF and added drop wise to lithium (tri-sec-butyl) borohydride in the THF at −50° C. After reaction for 2 hours at −50° C. the reaction was warmed to −10° C., water cautiously added, and the product, Compound 7, extracted with dichloromethane.

G. Final Work-up

On mild acid hydrolysis Compound 7 yields N-trifluoroacetyl-L-daunosamine, 8, which after p-nitrobenzoylation and halogenation, is suitable for coupling to anthracycline-type aglycones and the synthesis of anthracycline-type antibiotics as discussed below.

II. Synthesis of 1-Thio-Acosamine and Other Thio Sugars

The starting material for this synthesis is again the L-rhamnal enone 1. This synthesis is characterized by a Michael-type addition of an alkyl thiol under basic conditions which yields the S-alkyl thioglycoside 2-deoxy-3-ulose, Compound 9. Oximation with hydroxylamine produces Compound 10 which is directly acetylated to the di-O-acetate Compound 11. Again, by employing the borane-THF complex, stereospecific reduction of Compound 11 to an L-arabino (acosamine) derivative is achieved. The 1-thioacosamine glycoside is sequentially pertrifluoroacetylated and O-detrifluoroacetylated by treatment with methanol to yield S-alkyl N-trifluoroacetyl-1-thio-L-acosaminide, 12, in 60% overall yield from 1.

While the present invention has thioacosamines as one of its principal objects, this reaction sequence can be used to synthesize thio sugars in general. That is, it is envisioned that carbohydrate enones in general will add a thioalkyl group by Michael addition in accordance with the present invention.

The synthesis of the thio-acosamines is analogous to that of daunosamine and is accomplished under similar conditions. The reactions are illustrated using the thiobenzyl derivative, however, it will be apparent to those skilled in the art that other derivatives can be prepared by substituting other alkyl and substituted alkyl mercaptans for benzyl mercaptan in the Michael-type addition.

In another embodiment the Michael-type addition nucleophile is a metal salt of a sulfur substituted alkyl where the alkyl group is such that it can be readily removed under mild conditions to generate the thioalcohol upon glycosidation of the aglycone. Representative of these other reactants are potassium thio acetate and the potassium salt of benzyl mercaptan. The alkyl thiols and salts thereof used in the present invention are generally compounds in which the alkyl moiety may be unsubstituted or substituted by, for example, a phenyl group, a carboxyl group, etc. The objective is to use an alkyl group which can be readily removed when the sugar is used to synthesize the antibiotic as discussed below.

In the thioacosamine synthesis, the Michael-type addition is usually conducted by adding pyridine containing a few drops of triethylamine, or other tertiary amine such as tripropylamine or tri-n-butylamine, to an equimolar mixture of Compound 1 and this nucleophile, which for purposes of illustration is benzyl mercaptan. The reaction mixture is kept at room temperature for 1 hour.

Oximation by addition of hydroxylamine hydrochloride and a lower alcohol (e.g., methanol, ethanol) to the mixture is accomplished in 2 hours in a manner analogous to that already described.

Acetylation of the mixture with a mixture of equal volumes of pyridine and acetic anhydride yields Compound 11.

Compound 11 is stereospecifically reduced with lithium aluminum hydride in THF or, preferably, with borane-THF complex in THF, to yield the arabino compound as previously described. This intermediate is di-N,O-tri-fluoroacetylated in ethyl ether and then treated with methanol to cause cleavage of the O-ester, but not the N-amide. Birch reduction of the benzyl thioglycoside yields thioacosamine for subsequent reaction as discussed below.

III. Synthesis of Antibiotics

Anthracycline antibiotics can be prepared by coupling the amino sugars prepared as above with the aglycone by glycosidation of the 7-hydroxyl group of the aglycone after protecting the 3-amino group of the sugar. Several prior methods are suitable for reacting the sugar and aglycone to produce the antibiotic. Most notable are those of Acton, et al., *J. Med. Chem.* 17 (1974) 659. These workers reacted N-trifluoroacetyl-O-p-nitrobenzoyl-L-daunosaminyl bromide with daunomycinone in THF at reflux. The reaction was catalyzed by mercuric cyanide, mercuric bromide, and powdered 3 Å molecular sieve. After 2 days at reflux the product glycoside was isolated by column chromatography.

Of the aglycones to which amino sugars synthesized in accordance with the present invention may be coupled to produce useful or potentially useful products, daunomycinone, carminomycinone, adriamycinone, ε-rhodomycinone are representative.

Acton and co-workers (*J. Med. Chem*, 17 (1974, 659) reported the coupling of daunomycinone and a suitably protected daunosaminyl bromide to yield Adriamycin ™ hydrochloride by a modified Koenigs-Knorr reaction catalyzed by mercuric cyanide, mercuric bromide, and powdered 3 A molecular sieves. The reaction was conducted in refluxing tetrahydrofuran and generated only the desired α-L anomer. Similar routes to the glycosidation of adriamycinone were reported by Smith et al, *J. Am. Chem. Soc.* 98 (1976) 1969 and *J. Org. Chem.*, 42 (1977) 3653.

Fuchs, Horton and Weckerle, *Carbohydr. Res.*, (1977) C36 describe the glycosidation of daunomycinone with 3,4-di-O-acetyl-2-,6-dideoxy-α-L-lyxo-hexopyranosyl chloride. The reaction is conducted in anhydrous dichloromethane and catalyzed by yellow mercuric oxide and mercuric bromide. The glycoside is obtained in 84% yield. Similar work on the glycosidation of adriamycinone with the above L-lyxosyl chloride was reported by Horton and Turner, *Carbohydr. Res.* 77 (1979) C8.

El Khadem et al, *J. Med. Chem.*, 20 (1977) 957 have investigated the reaction between ε-rhodomycinone, an aglycone closely related to daunomycinone/adriamycinone, and 26 sugar halides. These reactions were done in refluxing THF and were catalyzed by mercuric cyanide, mercuric bromide, and powdered 3 A molecular sieves.

*J. Med. Chem.*, 19 (1976) 733 report a novel glycosidation of daunomycinone. They reacted daunomycinone and 1,2,3-trideoxy-4,6-di-O-p-nitrobenzoyl-3-trifluoro-acetamido-L-arabino-hex-1-enopyranose in benzene at 55° C. in the presence of a catalytic amount of p-toluenesulfonic acid. Only the α-L anomer was obtained by the acid-catalyzed glycal addition procedure. These modified glycosides are reported to be less active than daunomycin and doxorubicin but also considerably less toxic.

Aglycones may be prepared using several suitable prior techniques. The total synthesis of daunomycinone is disclosed by Wong et al., *Canad. J. Chem.* 51 (1973) 446. Suitable syntheses of tetracyclic aglycones are also disclosed in U.S. Pat. No. 4,070,382; Suzuki et al., *J. Org. Chem.* 43 (1978) 4159; Lee et al., *J. Org. Chem.*, 41

(1976) 2296 and Krohn et al., *Chem. Ber.* 112 (1979) 3453-3471.

Thioacosamine, prepared by Birch reduction of the precursor benzyl thioglycoside, may be coupled to adriamycinone/daunomycinone in either of two ways. The 1-thio-sugar may be coupled to the aglycon by reaction in trifluoroacetic acid, similar to a reaction described by Essery et al. *J. Med. Chem.*, 22 (1979) 1425, for the coupling of 3-aminocyclohexanethiol to carminomycinone. Alternatively, the parent antibiotic may be converted to its 7-bromo derivative by way of reactions described by Smith et al., *J. Org. Chem.*, 42 (1977) 3653. This benzylic bromide may be reacted with thioacosamine in the presence of a base such a pyridine or triethylamine to yield the desired product thioglycoside.

The invention will now be illustrated in more detail by the following examples in which the reaction sequences discussed above are reproduced. Unless otherwise indicated, all percents, parts and ratios are by weight.

EXAMPLE I

Preparation of Methyl 2,6-dideoxy-α-β-L-erythrohexopyranosid-3-ulose (compound 2)

A solution of compound 1 (900 mg) in 0.01 M methanolic sodium methoxide (120 ml) was kept at room temperature for 10 minutes, and then neutralized with AG 50 W-X12(H+) cation-exchange resin, Dowex resin from J. T. Baker, and evaporated to dryness to give colorless, syrupy product which was identified as compound 2 (940 mg., 83%, α:β ratio 15.1).

$[\alpha]_D^{25} -139°$ (c 0.31, methanol) lit. $[\alpha]_D^{25} -177.8°$ (c 1.,7, methanol) for a pure anomer.

N.m.r. Data (CDCl$_3$) 1.42 (d, 3H, $J_{5,6}$ 5 Hz, CH$_3$-5.), 2.60 dd, 1H, $J_{1e,2e}$ 1.5, $J_{2e,2a}$ 13.5 Hz, H-2e), 2.84 (dd, 1H, $J_{1e,2a}$ 4 Hz, H-2a), 3.6-4.1 (m, 2H, H-4 and H-5), 5.10 (dd, 1H, H-1e); for the contaminating (6-6.5%) anomer: 4.61 (dd, 1H, $J_{1a,2e}$ 8, $J_{1a,2e}$ 4 Hz, H-1a).

Elemental Analysis for C$_7$H$_{12}$O$_4$—Calculated: C, 52.49; H, 7.55; Found: C, 52.31; H, 7.53.

EXAMPLE 2

Preparation of Methyl 2,3,6-trideoxy-3-trifluoro acetamido-α-β-L-arabino-hexopyranoside Compound (5)

To a solution of Compound 2 (450 mg) in abs. methanol (5 ml) was added a solution of hydroxylamine in abs. methanol [10 ml prepared from hydroxylamine hydrochloride (1.17 g) and potassium hydroxide (975 mg)]. After storage at room temperature for 4 hours, thin layer chromatography showed that compound 2 had disappeared. The reaction mixture was evaporated to dryness to give a syrupy residue (400 mg) consisting of the oxime compound 3 (R$_F$0.44) and two minor components (less than 5% R$_F$ 0.2 and 0.15).

The oxime 3 was acetylated by treating it with a mixture of equal volumes of acetic anhydride and pyridine. To obtain pure syrupy diacetate, compound 4. This was reduced with borane in THF, with a 10 molar excess of the BH$_3$-THF reagent. After working up of the reaction mixture, followed by trifluoroacetylation using (CF$_3$CO)$_2$O in ether, O-deacylation in methanol gave compound 5 which was recrystallized from acetone-petroleum ether. Yield 67%; m.p. 195°-96° C. (subl.)

$[\alpha]_D^{21} -110.8°$ (C 0.6, methanol). lit. m.p. 195°-97° C. $[\alpha]_D^{21} -110°$ (C, 0.2, methanol).

EXAMPLE 3

Preparation of methyl 2,3,6-trideoxy-3-trifluoroacetamido-α-β-L-threo-hexopyranoside-4-ulose (Compound 6)

To a solution of the CrO$_3$:2 pyridine complex (4 mM) in dichloromethane (15 ml), 257 mg (1 mM) of Compound 5 and 0.377 ml (4 mM) acetic anhydride were added. The mixture was stirred at room temperature for 20 min. and then worked up by pouring the reaction mixture onto a silica gel column (ethyl acetate eluent) over the top of which is a volume of ethyl acetate to precipitate insoluble chromium compounds. Elution with chloroform gives 203 mg (79.4%) of Compound 6, an approximately 1:1 mixture of the α and β anomers as determined by 1H-NRM examination), m.p. 62°-64° C.

IR$\nu_{max}$: 1740 cm$^{-1}$ (ketone C=0); 1700 cm$^{-1}$ (amide I), 1500 cm$^{-1}$ (amide II).

EXAMPLE 4

Preparation of 2,3,6-Trideoxy-3-trifluoroacetamido-L-lyxo-hexopyranose(N-trifluoroacetyl-L-daunosamine) (Compound 8)

A solution of Compound 6 (65 mg) in dry THF (3 ml) was added to 1 ml of 1 M lithium (tri-sec-butyl) borohydride in THF at −50° C. After stirring for 2 hours water (60 ml) was added at −10° C. and the pH was adjusted to 4. The reaction mixture was extracted with CH$_2$Cl$_2$, the organic layer was dried, concentrated and the residue was hydrolyzed with 20% (v/v) acetic acid to obtain 34 mg (55%) of Compound 8 m.p. 146°-148° C. Lit., m.p. 146°-147° C.

EXAMPLE 5

Benzyl 4-O-acetyl-1-thio-2,3,6-trideoxy-α-L-erythrohexopyranoside-3-ulose oxime acetate (Compound 11)

To a mixture of 1,5-anhydro-2,6-dideoxy-L-erythrohex-1-en-3-ulose, (Compound 1) (0.64 g; 5 mM) and benzyl mercaptan (0.621 g; 5 mM), a 0.5 ml aliquot of 10 ml pyridine containing 5 drops of triethylamine was added. After being kept at room temperature for 1 hour, thin layer chromatography indicated that almost all of the starting material had disappeared. Hydroxylamine hydrochloride (350 mg) and abs. methanol (2.5 ml) were added and the mixture was shaken until all of the reagent dissolved. The formation of the oxime (Compound 10) was complete within two hours. The mixture was evaporated and the residue was acetylated with acetic anhydride (3 ml) in pyridine (3 ml) to obtain homogeneous syrupy Compound 11 (1.156) g; 66%).

NMR (90 MHz in CDCl$_3$): 1.20 (d, 3H, CH-$_3$-5); 2.06 and 2.09 (2s, 6H, OAc), 2.67 (m, 1H, H-2a); 3.25 (m, 1H, H-2e, $J_{1,2e}$-3H$_2$); 7.35 (5Ha, aromatic).

EXAMPLE 6

Benzyl 1-thio-2,3,6-trideoxy-3-trifluoroacetamido-α-L-arabino-hexopyranoside—(Compound 12) and its 4-0-acetate A. LiAlH$_4$ reduction of Compound 11

To a solution of Compound 11 (372 mg) in THF 220 mg of LiAlH$_4$ was added in portions and the mixture was refluxed for six hours. After working up the mixture in the usual way the resulting mixture was trifluoroacetylated, O-deacetylated and then acetylated. The reduction product was trifluoroacetylated with trifluoroacetic acid anhydride in ether and O-deacylated by treatment with methanol. The resulting N-trifluoroacetamido derivative was O-acetylated by treatment with a mixture of equal volumes of acetic anhydride and pyridine. The product mixture was subjected to column chromatography to obtain the acetate in 20% yield.

B. Borane reduction of Compound 11

Compound 11 (770 mg) was dissolved in dry THF (1 ml) and cooled to 0° C. A solution of borane in THF (1 M, 1 ml) was added over a period of 30 minutes. The mixture was stirred at 0°-5° C. for 1 hour, refluxed for 1.5 hours, and then allowed to stand at room temperature for 18 hours. The solution was cooled (0° C.) and to it was added 20% sodium hydroxide slowly (1 ml). The mixture was refluxed for 4 hours, the phases separated, the aqueous phase extracted with ethyl ether. The combined organic phases were dried and the product was isolated by evaporation of the solvent. The product was then trifluoroacetylated with trifluoroacetic anhydride and then O-deacylated with methanol. The crude product 12 was recrystallized from ether-petroleum ether to give analytically pure product in 60% yield, m.p. 154°-155° C.; $[\alpha]_D^{21} -272°$ (C 0.85, methanol)].

C.

The 4-O-acetate of compound 12 was prepared by treating Compound 12 with a mixture of equal volumes of acetic anhydride and pyridine followed by extraction with chloroform or dichloromethane; m.p. 165°-166°, $[\alpha]_D^{21} -290°$ (C 0.8, methanol). NMR (200 MHz) examinations of both Compound 12 and its acetate confirmed the proposed structures.

EXAMPLE 7

Daunomycinone (100 mg), mercuric cyanide (500 mg), mercuric bromide (250 mg) and powdered 3 Å molecular sieve (1.1 g) were put into THF (30 ml) and stirred at 50°-55° C. for 2-3 hours. Three molar equivalents of 2,3,6-trideoxy-4-O-p-nitrobenzoyl-3-trifluoroacetamido-α-L-lyxohexopyranosyl chloride in methylene chloride (2 ml) were added at 0,4, and 24 hours while the temperature was maintained at 50°-55° C. The chloro sugar was prepared by bubbling dry HCl into a suspension of 2,3,6-trideoxy-1,4-di-O-p-nitrobenzoyl-3-trifluoro-acetamido-α-L-lyxohexopyranose (135 mg) in methylene chloride (4 ml) at 0° C. for 3-5 minutes. The mixture was allowed to stand at 25° C. for 10-15 minutes, filtered to remove the insoluble p-nitrobenzoic acid, and evaporated. The residue was dissolved in methylene chloride (2 ml) and added to the reaction mixture. Additional mercuric cyanide (500 mg), mercuric bromide (250 mg) and powdered 3 Å molecular sieve (0.5 g) were added at 3-5 hours. The total reaction time was 26 hours. The reaction mixture was filtered, the solids washed with THF, and the combined filtrates were evaporated. The residue was triturated with chloroform (70 ml) and filtered. The filtrate was washed with 30% potassium iodide (2×25 ml) and water (1×50 ml), dried and evaporated. The residue was subjected to preparative thin layer chromatography to yield 145 mg of the desired product.

EXAMPLE 8

S-benzyl thioacosaminide (0.3 mmole) was dissolved in liquid ammonia (10 ml) containing THF (1 ml), and to the stirred solution was added, in portions, sodium metal until a blue color persisted. Following the addition of ammonium chloride, ammonia was evaporated under a nitrogen atmosphere. The solid residue was dissolved in trifluoroacetic acid (5 ml) and filtered to remove salts. Daunomycinone (0.2 mmole) was added to the filtrate and the solution was stored for 17 hours at 40°-50° C. The solvent was evaporated under reduced pressure and the residue was dissolved in methylene chloride which was then extracted with aqueous hydrochloric acid (pH 3-4, 4×20 ml). The acidic extracts were adjusted to pH 8.0 with dilute sodium hydroxide and the product extracted into methylene chloride. This organic phase was washed with saturated sodium chloride and dried over anhydrous sodium sulfate and filtered. The filtrate was evaporated to yield the product thioglycoside as a red solid (20% yield).

While the invention has been described in detail and by reference to specific embodiments thereof, it will be apparent to those skilled in the art that numerous variations and modifications are possible without departing from the spirit of the invention as defined in the following claims.

What is claimed is:

1. A process for producing a thiohexopyranoside which comprises reacting a hex-1-en-3-ulose with an alkylthiol or a salt thereof in the presence of a base so as to effect a Michael Addition of a thioalkyl group at the 1-position of said hex-1-en-3-ulose.

2. The process of claim 1 wherein said hex-1-en-3-ulose is 1,5-anhydro-2,6-dideoxy-α-L-erythro-hex-1-en-3-ulose.

3. The process of claim 2 wherein said alkyl thiol or salt thereof is selected from the group consisting of benzyl mercaptan, potassium thioacetate, and the potassium salt of benzyl mercaptan.

4. A process for producing L-thioacosamine derivatives which comprises:
   oxidizing L-rhamnal to produce 1,5 anhydro-2,6-dideoxy-α-L-erythro-hex-1-en-3-ulose,
   reacting said 1,5 anhydro-2,6-dideoxy-α-L-erythro-hex-1-en-3-ulose with an alkylthiol or salt thereof in the presence of a strong base to produce alkyl 2,6-dideoxy-1-thio-α-L-erythro-hexopyranosid-3-ulose by Michael addition,
   reacting said alkyl 2,6-dideoxy-1-thio-α-L-erythro-hexopyranosid-3-ulose with hydroxylamine to introduce an oximino group at the 3-position;
   reacting the resultant 3-oximino compound with acetic anhydride to produce the di-O-acetyl compound;

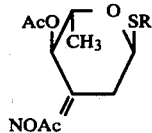

and stereospecifically reducing said di-O-acetyl compound with borane in tetrahydrofuran to convert the 3-oximino group to a 3-amido group of the arabino configuration.

5. The process of claim 4 wherein said alkyl thiol is benzyl mercaptan and said base is pyridine.

6. A process for producing L-acosamine derivatives comprising:
oxidizing L-rhamnal to produce 1,5-anhydro-2,6-dideoxy-α-L-erythro-hex-1-en-3-ulose;
reacting 2,6-dideoxy-α-L-erythro-hex-1-en-3-ulose with sodium methoxide in methanol to produce the compound methyl 2,6-dideoxy-α-L-erythro-hexopyranosid-3-ulose,
reacting the resultant methyl 2,6-dideoxy-α-L-erythro-hexopyranosid-3-ulose with hydroxylamine to introduce an oximino group at the 3-position,
reacting the resultant 3-oximino compound with acetic anhydride to produce the di-O-acetyl compound

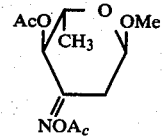

and stereospecifically reducing the resultant di-O-acetyl compound with borane in tetrahydrofuran to convert the 3-oximino group to a 3-amido group of the arabino configuration.

* * * * *